United States Patent
Robinson (10) Patent No.: US 9,278,007 B2
(45) Date of Patent: Mar. 8, 2016

(54) PROSTHETIC INTERVERTEBRAL DISCS HAVING CAST END PLATES AND METHODS FOR MAKING AND USING THEM

(75) Inventor: Janine C. Robinson, Half Moon Bay, CA (US)

(73) Assignee: SPINAL KINETICS, Inc., Sunnyvale, CA (US)

(*) Notice: Subject to any disclaimer, the term of this patent is extended or adjusted under 35 U.S.C. 154(b) by 1403 days.

(21) Appl. No.: 11/528,175

(22) Filed: Sep. 26, 2006

(65) Prior Publication Data
US 2008/0077244 A1  Mar. 27, 2008

(51) Int. Cl.
*A61F 2/44* (2006.01)
*A61F 2/30* (2006.01)

(52) U.S. Cl.
CPC .............. *A61F 2/442* (2013.01); *A61F 2/3094* (2013.01); *A61F 2/30742* (2013.01); *A61F 2002/30133* (2013.01); *A61F 2002/30448* (2013.01); *A61F 2002/30495* (2013.01); *A61F 2002/30563* (2013.01); *A61F 2002/30738* (2013.01); *A61F 2002/30884* (2013.01); *A61F 2002/4495* (2013.01); *A61F 2220/005* (2013.01); *A61F 2220/0025* (2013.01); *A61F 2230/0015* (2013.01)

(58) Field of Classification Search
USPC ........ 623/17.11–17.16; 606/61, 246, 279, 76, 606/78, 331, 907, 910
See application file for complete search history.

(56) References Cited

U.S. PATENT DOCUMENTS

| | | | |
|---|---|---|---|
| 3,867,728 A | 2/1975 | Stubstad et al. | |
| 4,309,777 A | 1/1982 | Patil | |
| 4,623,574 A | 11/1986 | Harpell et al. | |
| 4,759,769 A | 7/1988 | Hedman et al. | |
| 4,911,718 A | 3/1990 | Lee et al. | |
| 4,932,969 A | 6/1990 | Frey et al. | |
| 5,002,576 A | 3/1991 | Fuhrmann et al. | |
| 5,039,519 A | 8/1991 | Inoue et al. | |
| 5,171,281 A | 12/1992 | Parsons et al. | |
| 5,221,431 A | 6/1993 | Choe et al. | |
| 5,221,432 A | 6/1993 | Choe et al. | |
| 5,314,477 A | 5/1994 | Marnay | |
| 5,370,697 A | 12/1994 | Baumgartner | |
| 5,456,722 A | 10/1995 | McLeod et al. | |
| 5,458,642 A | 10/1995 | Beer et al. | |
| 5,534,028 A * | 7/1996 | Bao et al. ................... | 623/17.16 |
| 5,534,030 A * | 7/1996 | Navarro et al. ............ | 623/17.15 |
| 5,545,229 A | 8/1996 | Parsons et al. | |
| 5,609,634 A | 3/1997 | Voydeville | |
| 5,827,328 A | 10/1998 | Buttermann | |
| 6,063,121 A * | 5/2000 | Xavier et al. .............. | 623/17.15 |

(Continued)

FOREIGN PATENT DOCUMENTS

WO  WO2005/011523  2/2005

OTHER PUBLICATIONS

Hudgins, Robert, "Development and Characterization of a Prosthetic Intevertebral Disc," Thesis presented to the Academic Faculty, Georgia Institute of Technology (Nov. 98).

(Continued)

*Primary Examiner* — David Isabella
*Assistant Examiner* — Christine Nelson
(74) *Attorney, Agent, or Firm* — E. Thomas Wheelock (57) ABSTRACT

This description deals with a medical device, specifically a prosthetic intervertebral disc having a compressible core and at least one cast, polymeric end plate.

18 Claims, 4 Drawing Sheets

(56) References Cited

U.S. PATENT DOCUMENTS

| | | |
|---|---|---|
| 6,113,638 A | 9/2000 | Williams et al. |
| 6,156,067 A | 12/2000 | Bryan et al. |
| 6,258,125 B1 | 7/2001 | Paul et al. |
| 6,264,695 B1 | 7/2001 | Stoy |
| 6,402,785 B1 | 6/2002 | Zdeblick et al. |
| 6,419,704 B1 | 7/2002 | Ferree |
| 6,419,706 B1 | 7/2002 | Graf |
| 6,436,137 B2 | 8/2002 | Wang et al. |
| 6,447,543 B1 * | 9/2002 | Studer et al. .............. 623/17.11 |
| 6,527,803 B1 | 3/2003 | Crozet et al. |
| 6,527,804 B1 | 3/2003 | Gauchet et al. |
| 6,533,818 B1 | 3/2003 | Weber et al. |
| 6,582,466 B1 | 6/2003 | Gauchet |
| 6,582,468 B1 | 6/2003 | Gauchet |
| 6,626,943 B2 * | 9/2003 | Eberlein et al. ............ 623/17.15 |
| 6,626,944 B1 | 9/2003 | Taylor |
| 6,645,248 B2 | 11/2003 | Casutt |
| 6,656,224 B2 | 12/2003 | Middleton |
| 6,682,562 B2 | 1/2004 | Viart et al. |
| 6,692,495 B1 | 2/2004 | Zacouto |
| 6,726,721 B2 | 4/2004 | Stoy et al. |
| 6,733,533 B1 | 5/2004 | Lozier |
| 6,733,535 B2 | 5/2004 | Michelson |
| 6,746,485 B1 | 6/2004 | Zucherman et al. |
| 6,749,635 B1 | 6/2004 | Bryan |
| 6,827,740 B1 | 12/2004 | Michelson |
| 6,827,743 B2 | 12/2004 | Eisermann et al. |
| 7,025,787 B2 | 4/2006 | Bryan et al. |
| 7,060,097 B2 | 6/2006 | Fraser et al. |
| 7,074,240 B2 | 7/2006 | Pisharodi |
| 7,147,665 B1 | 12/2006 | Bryan |
| 7,166,130 B2 | 1/2007 | Ferree et al. |
| 7,220,282 B2 * | 5/2007 | Kuslich et al. ............. 623/17.16 |
| 7,229,441 B2 | 6/2007 | Trieu et al. |
| 7,291,150 B2 | 11/2007 | Graf |
| 7,309,357 B2 | 12/2007 | Kim et al. |
| 2002/0026244 A1 | 2/2002 | Trieu |
| 2002/0111687 A1 | 8/2002 | Ralph et al. |
| 2002/0128714 A1 | 9/2002 | Manasas et al. |
| 2003/0028251 A1 | 2/2003 | Mathews |
| 2004/0006343 A1 | 1/2004 | Sevrain |
| 2004/0143332 A1 | 7/2004 | Krueger et al. |
| 2005/0021146 A1 | 1/2005 | de Villiers et al. |
| 2005/0060036 A1 | 3/2005 | Schultz et al. |
| 2006/0129239 A1 | 6/2006 | Kwak |
| 2006/0149381 A1 * | 7/2006 | Kim .......................... 623/17.13 |
| 2007/0032875 A1 | 2/2007 | Blacklock et al. |
| 2007/0168033 A1 | 7/2007 | Kim et al. |
| 2007/0179621 A1 | 8/2007 | McClellan, III et al. |

OTHER PUBLICATIONS

Takahata et al. "Bone Ingrowth Fixation of Artificial Intervertebral Disc Consisting of Bioceramic-coated Three-dimensional Fabric," SPINE, vol. 28, No. 7, pp. 637-644.

* cited by examiner

PROSTHETIC INTERVERTEBRAL DISCS HAVING CAST END PLATES AND METHODS FOR MAKING AND USING THEM

FIELD

This description deals with a medical device, specifically a prosthetic intervertebral disc having a compressible core and at least one cast end plate.

BACKGROUND

The intervertebral disc is an anatomically and functionally complex joint. The native intervertebral disc is made up of three component structures: (1) the nucleus pulposus; (2) the annulus fibrosus; and (3) the vertebral endplates. The biomedical composition and anatomical arrangements within these component structures are related to the biomechanical function of the disc.

The spinal disc may be displaced or damaged due to trauma or disease. As a result of such displacement or damage, the nucleus pulposus may herniate and protrude into the vertebral canal or intervertebral foramen. That deformation is commonly known as a herniated or "slipped" disc. The protrusion may press upon one or more of the spinal nerves exiting the vertebral canal through the partially obstructed foramen, causing pain or paralysis in the area of the spinal nerve's influence.

One method of alleviating this condition involves surgically removing the involved disc and fusing the two adjacent vertebrae. In this procedure, the removed disc is replaced by a spacer and secured to the neighboring vertebrae by screws, plates, and rods. Although "spinal fusion" evidences excellent short-term results, long-term studies show that the procedure eventually leads to degenerative changes in the spine, particularly at adjacent still flexible, spinal discs. As a result of the fused segment's increased stiffness, adjacent discs incur increased motion and stress. In the long term, this change in the mechanics of the spine causes those adjacent discs to degenerate.

Prosthetic intervertebral discs are now used as alternatives to spinal fusion. Various artificial intervertebral disc designs are extant; many share the goal of mimicking the kinematics and load-sharing properties of the natural intervertebral disc. Two such design categories are ball-and-socket joint type discs and elastic rubber or elastomeric discs.

Artificial discs of the ball-and-socket type usually include a pair of concave metal plates and a rounded core. One of the concave metal plates is attached to the upper vertebra and the other is attached to the lower vertebra. The concavities within the metal plates cooperate with and will rotate with respect to the rounded core. The ball-and-socket type disc allows free rotation between the adjacent vertebrae between which the disc is installed. Such discs do not share any of the load placed on the spine as the spine bends.

Such ball-and-socket discs have very high stiffness in the vertical (or compressive) direction. That is to say that they are more incompressible than the natural disc. As a result, although these prosthetic discs allow flexion of the spine where a fused disc does not, the structure of these discs still causes adjacent spinal discs to absorb extra compressive loads and still allows eventual and early degeneration of those discs.

Another common artificial disc design includes an elastic rubber or elastomeric polymer body embedded between a pair of metal plates. The disc is introduced into the surgically emptied region between two adjacent vertebrae by affixing the two metal plates to those two vertebrae. In this design, the elastomeric polymer body is bonded to a rough, porous interface surface on each of the metal plates. This disc design is able both to absorb vertical, compressive shocks and to bear loads in that direction. However, the interface between the elastomeric polymer body and the metal plates is subject to peeling or severance due to the nature of the junction.

The prosthetic devices described here generally include a compressible core, perhaps containing gel or polymeric materials, and at least one cast end plate, typically polymeric and typically binding or affixed to a structural component that is peripheral to that core. The casting material may also be structural in nature, e.g., epoxies and the like.

SUMMARY

This description includes prosthetic intervertebral discs and methods for making and using such discs. Our prosthetic discs include upper and lower end plates, at least one of which is a cast, polymeric structure and which plate or plates typically bind a component that is peripheral to a compressible core member situated between those two end plates. The component that is peripheral to the core may be a fiber assembly, a fiber-containing membrane, a wire assembly, stent-like structure, fabric, or the like that may be associated with one or more anchoring components held in position by the end plate or plates. That peripheral core component may be an independent structure or may be integrated with the core.

Our described prosthetic disc may include top and bottom plates typically separated by a compressible core. The core may comprise one or more hydrogels or elastomers or both. The core may comprise a variety of different configurations comprising, e.g., single materials having a single composition, single materials having varied composition (perhaps with a nuclear region approximating the size the nucleus pulposus), single materials having regions of different physical characteristics, multiple compositions, structural variations having fabric-defined volumes, baffled regions, fiber-infused gel or elastomeric regions, and the like. The described disc may comprise a subcomponent fiber-wrapped compressible core, variously made of a "neat" filling material or comprising a subcomponent having a fiber-wrapped compressible core, where the core, before wrapping, includes upper and lower plates that are included within that wrapping. The plates may include extensions or other attachments suitable for directly (or indirectly) attaching to the two adjacent vertebrae. The cores may be preformed or formed in place.

The described prosthetic discs may be used with separate vertebral body fixation elements or may include integrated vertebral body fixation elements. The prosthetic discs may be included in kits.

BRIEF DESCRIPTION OF THE DRAWINGS

The Figures are not necessarily drawn to scale. Some components and features in the drawings may be exaggerated for clarity.

DESCRIPTION

The description of a particular variation is not limited to the specifics of that particular variation, as such may, of course, vary. The terminology in this description has been chosen only for the purpose of explaining and describing particular variations, and is not intended to be limiting, since the scope of the description will be limited only by the appended claims.

Unless defined otherwise, all of the technical and scientific terms found in the text have the same meaning as would be commonly understood by one of ordinary skill in the medical device art. All publications mentioned in this description are incorporated by reference to disclose and to describe the methods or materials in connection with which the publications are cited.

As used in the text and in the appended claims, the singular forms "a", "an", and "the" include plural referents unless the context clearly requires otherwise.

It is our intention that, in this description, each discrete component and feature that may be separated from a described device may be combined into or with other variations of that device.

Described herein are prosthetic intervertebral discs and methods for making and using them. The prosthetic discs include top and bottom plates separated by a compressible element.

At least one of those upper and lower plates comprises a cast or molded, polymeric structure. Those plate or plates typically are affixed to or bind a peripheral core component, a structural element that is peripheral to the compressible core member situated between those two end plates.

The compressible element may include one or more annular elements or regions and a nuclear region or element. The compressible element or core is often configured to mimic the range of motion, compressibility, axis of rotation, and springiness of natural vertebral discs. The interior of the compressible element may variously comprise elastomeric materials or polymeric gels having a single density or containing varying materials having several different densities are including flow restrictors such as baffles or the like. The interior of the compressible element may also comprise a portion that is a wrapped or woven to include other materials that cooperate to mimic the motion of a natural disc. The interior of the compressible element in these variations may also be molded prior to placement in the boundary membranes The described prosthetic discs may be employed with separate vertebral body fixation elements or they may include integrated body fixation elements.

As mentioned above, the device we describe here and is a prosthetic intervertebral disc. By the term "prosthetic intervertebral disc," we mean an artificial device that is configured or shaped in such a way that it may be used as a replacement for an intervertebral disc in the spine of a vertebrate, e.g., a mammal such as a human. Our described disc may be varied in size, width, thickness, shape, and the like, to generally match the removed natural disc or be appropriate for the opening left by its removal. That is to say that our prosthetic intervertebral disc has dimensions that permit it to substantially occupy the space between two adjacent vertebral bodies that exists when the naturally occurring disc between the two vertebrae has been removed.

By the term "substantially occupy," we mean that the prosthetic intervertebral disc occupies at least 75% of the void disk space. In general, our prosthetic intervertebral discs are roughly bean-shaped structures when viewed from above or below and have the approximate shape of the naturally occurring intervertebral discs that they replace.

In most of our variations, the prosthetic intervertebral disc ranges in size, front to back, from about 5 mm to about 50 mm, perhaps from about 10 mm to about 45 mm or 10 to 35 mm. The width of the disc ranges, side to side, from about 2 mm to about 50 mm, perhaps from about 10 mm to about 35 mm. The height of the disc ranges from about 2 mm to about 15 mm, perhaps from about 5 mm to about 12 mm. Often, the top end plate is not parallel to the bottom end plate. The thickness of the compressible element may vary, but generally ranges in thickness from about 1 mm to about 12 mm, including from about 3 mm to about 10 mm.

The described prosthetic intervertebral discs may include an upper (or top) and a lower (or bottom) end plate, where the upper and lower endplates are separated from each other by the compressible element. Ideally, the combination of the endplates and the compressible element provides a prosthetic disc that functionally mimics the operation of a natural spinal disc.

Figure 1:
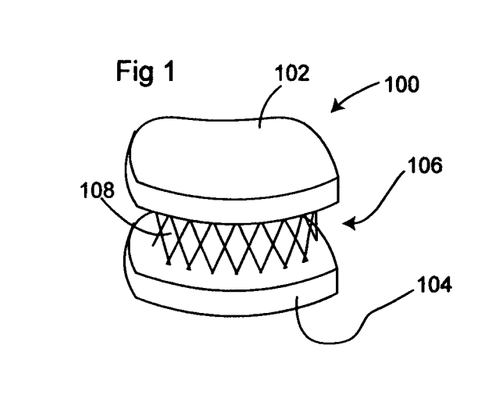
FIGS. 1 and 2 are perspective views of variations of our prosthetic intervertebral disc that may be used with separate vertebrae fixation components.

FIG. 1 shows a front perspective view of a first variation of our prosthetic intervertebral disc 100. Visible in this view are an upper (or top) end plate 102, and a lower end plate 104. The compressible element 106 may be seen between the upper plate 102 and lower end plate 104. It should be observed that this view of the prosthetic intervertebral disc 100 provides a somewhat bean-shaped visage similar in view to a natural disc.

The compressible element 106 seen in FIG. 1 includes one or more layers of fibers 108 that form a peripheral core member. These fibers may be pre-stressed or "biased" to provide a variety of translational effects during movement of the disc after implantation. In some variations of our disc, such fibers may be encased in a polymeric covering forming a membrane structure or may be integrated into the center member of the core.

As will be explained in greater detail below, the fibers 108 forming the peripheral core member may be affixed to or be cast into one or more of the cast, polymeric plates 102, 104.

The fibrous elements may be made up of one or more fibers. Useful fiber materials generally have a high modulus of elasticity, e.g., at least about 50 MPa, such as at least about 250 MPa, perhaps at least about 100 MPa, or about 500 MPa. The fibers are generally elongate fibers having a diameter in the range of from about 0.2 mm to about 1.0 mm, such as about 0.3 mm to about 0.8 mm. The length of each individual fiber making up a fibrous component may range from about 0.5 m to about 20 m, such as from about 1 m to about 3 m. Suitable fiber materials include polyesters (e.g., Dacron and the Nylons), polyolefins such as polyethylene and polypropylene, polyaramids such as Kevlar, carbon fibers, glass fibers, polyethylene terephthalate, acrylic polymers, methacrylic polymers, polyurethane, polyurea, halogenated polyolefins, vinylic polymers, polyphosphazene, polysiloxanes, and the like.

The fibers or fibrous elements may be made up of one or more fibers wound around one or more regions of the top or bottom plates and may make up a variety of different configurations. For example, the fibers may be wound in a pattern that has an oblique orientation to simulate the annulus of intact disc. The number of layers of wound fiber may be varied to achieve mechanical properties similar to an intact, normal disk. Where desired, compliancy of the structure may be reduced by including a horizontal winding configuration.

The windings of the various layers of fiber may be placed at varying angles from each other where an angle for each layer may be selected to provide a configuration best mimicking a natural disc. Additionally, the tension placed on the fibers of each layer may be the same or varied. Further, the density of the fibers, number of layers, frequency of winding, the wrapping angle of each fiber layer, and the like, may each be selected to approach or to mimic the mechanical properties of a natural intervertebral disc.

Figure 2:
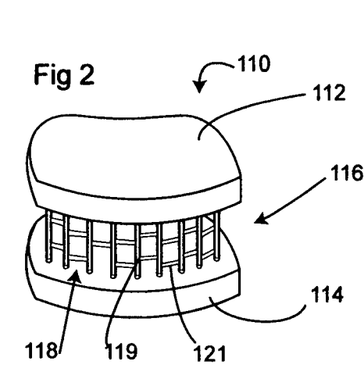

FIG. 2 shows a front perspective view of another variation of our prosthetic intervertebral disc 110. An upper (or top) end plate 112 and a lower end plate 114 may also be seen. The compressible element 116 may be seen between the upper plate 112 and lower end plate 114. In this variation, the peripheral core member 118 comprises a stent-like member that may be affixed to or be cast into one or more of the cast, polymeric plates 112, 114. Although the specific form of such metallic or polymeric stent-like peripheral core member structures is left to the designer, the structure shown is a schematic depiction of a structure having longitudinal wire or columnar segments 119 and wire crossing segments 121. The materials of construction, relative cross-sections, number of, and spacing of the longitudinal 119 and crossing segments 121 of such a structure sets the compressibility of the structure and its twisting characteristics. As noted above, the depicted stent-like structure 118 is intended only to be an example of the inclusion of such a structure as a peripheral core member. Many such shapes are suitable, including those having wire-like components, sheet components, components with specifically longitudinally compressible regions, components having regions that compress or squeeze the inner core to affect the biomechanical characteristics of the core during spinal motion, components having longitudinally springy regions, etc.

Additional specific disclosure relating to the cast end plate or plates will be provided below.

The variations shown in FIGS. 1 and 2 do not have specifically depicted features designed directly to affix the end plates (102, 104 in FIGS. 1 and 112, 114 in FIG. 2) to vertebrae in the spine. However, the depicted end plates may be configured to promote bone ingrowth or to provide other suitable spinal fixation features.

Figure 3:
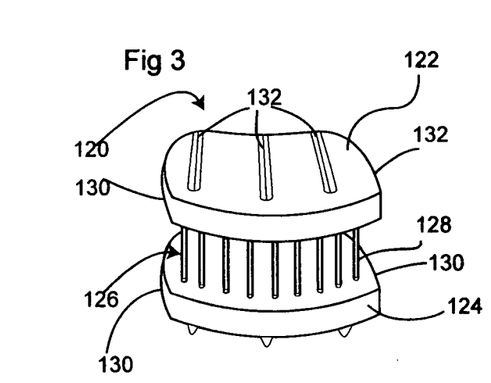
FIG. 3 is a perspective view of a variation of our prosthetic intervertebral disc that includes integral vertebrae fixation components.

FIG. 3 shows a perspective view of a variation of our prosthetic disc 120, in this case, having integrated features suitable for attaching the prosthetic disc to adjacent vertebrae in a patient's spine. The depicted prosthetic disc assembly 120 includes an upper end plate 122, a lower end plate 124, and a compressible core 126 with a peripheral core member 128 that comprises one or more fibers. The ends of the peripheral core member 128 are affixed to at least one of the upper end plate 122 and lower end plate 124. At least one of the upper end plate 122 and lower end plate 124 is cast or molded. The shape and features of the securing or attachment features utilized in the FIG. 3 variation, i.e., the shaped sides 130 and the barbed keel or fin members 132, are described in greater detail, for instance, in U.S. patent application Ser. No. 10/903, 276, filed Jul. 30, 2004, the entirety of which is incorporated by reference.

Figure 4:
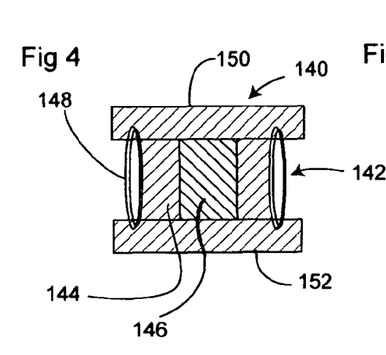
FIGS. 4 and 5 are cross-sectional side views of two variations of our prosthetic intervertebral disc.
Figure 5:
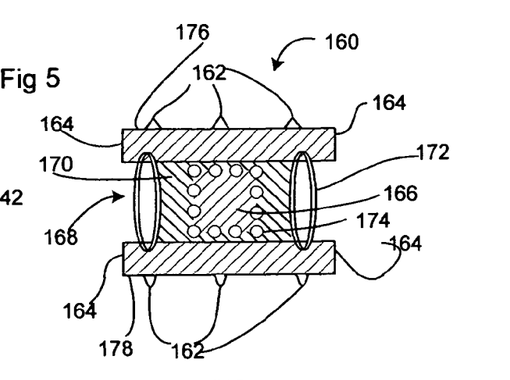

FIGS. 4 and 5 are cross-sectional views of, respectively, prosthetic discs of the general types shown in FIGS. 1 and 3.

FIG. 4 shows a variation of our prosthetic disc 140 having a central core assembly 142 comprising an annular core member 144, a central core member 146, and having an outer or peripheral core member 148. In this variation, annular core member 144 and central core member 146 are depicted to be elastomeric and may be assembled or otherwise integrated prior to placement in the resulting disc assembly. The peripheral core member 148 is shown to be adherent to and cast into both the upper end plate or member 150 and the lower end plate or member 152. The peripheral core member 148 is further shown to be a woven fibrous assemblage that extends from and between the upper end member 150 and the lower end member 152.

FIG. 5 shows a further variation of our prosthetic disc 160 that includes optional integral, vertebral attachment components (e.g., keel members 162) and attachment features (e.g., shaped sides 164) and a liquid or gel central core member 166. The central core assembly 168, in addition to comprising the central core member 166 includes an annular core member 170, and an outer or peripheral core member 172. In this variation, annular core member 170 may be elastomeric or gel. Central core member 166 is depicted to be an enclosed gel or liquid, enclosed by a fibrous or fiber-containing membrane 174, although the central core member may be elastomeric. The components of the central core assembly may be assembled or otherwise integrated prior to placement in the resulting disc assembly.

The peripheral core member 172 is shown to be adherent to and cast into both the upper end member 176 and the lower end member 178. The peripheral core member 172 is further shown to be a woven fibrous assemblage that extends from and between the upper end member 176 and the lower end member 178.

Figure 6:
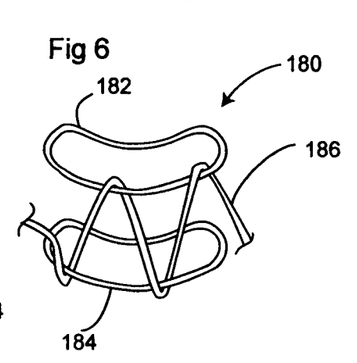
FIG. 6 is a schematic perspective view of a partially wound, peripheral core member showing anchoring components that may be cast into the end plates.

FIG. 6 shows a schematic representation of a portion of a peripheral core member 180. The peripheral core member 180 includes a pair of bead rings 182, 184 that are used both to provide a site for wrapping or weaving a fiber 186 back and forth across those rings and form an open ended structure and to provide a "bead" useful in anchoring the peripheral core member (as shown, for instance, in FIG. 8) in the respective end members or plates.

Figure 7:
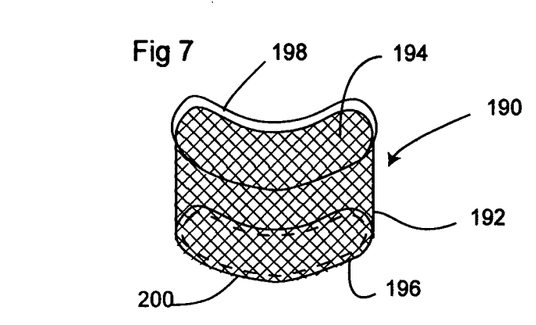
FIG. 7 is a perspective view of a peripheral core member.
Figure 14:
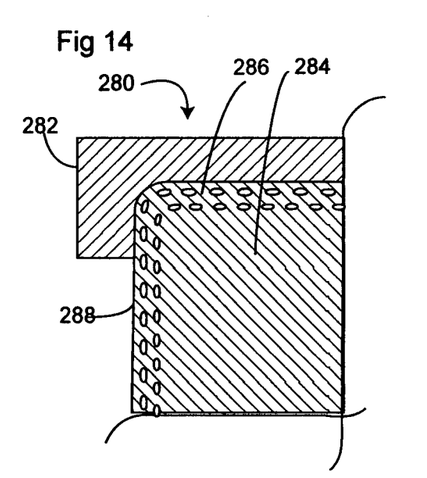

FIG. 7 shows a perspective view of a peripheral core member 190 comprising a fiber-containing membrane or fabric 192 and having an upper opening 194 and a lower opening 196. The peripheral core member 190 is shown to have optional foldable flaps 198, 200 that may be folded around bead members (as shown in FIG. 14), if so desired, in anchoring the peripheral core member 190 in the cast end plate or plates.

Although a single fabric tube may be provided in place of the wound fibers, two or more tubes of fabric may be provided between and interconnecting the upper and lower endplates. This latter structure creates an assembly of two or more concentric layers of fabric tubing. The concentric tubes may be terminated by collecting each tubing end together and crimping or sewing them together, then affixing the collected ends to the upper and lower endplates. Each fabric tube may be formed from the same fabric or formed from fabrics of material different from the other tubes (e.g., PET, PE, PTFE, polyamides, etc.), or from a fabric having different material properties. Such structures provide the ability to construct prosthetic discs having a range of performance characteristics.

FIGS. 8-15 show cutaway views of cast end plates showing a number of affixed or anchored peripheral core member variations.

By the term "cast," we mean that the referred-to component or subcomponent is at least partially produced from one or more materials that are flowable and that form such a component or subcomponent comprising the one or more materials in a non-flowable form, while in contact with another component of the prosthetic disc. The produced cast component may be substantially rigid, may be flexible, may be integrated with one or more other components of the prosthetic disc, or may be an independent component in our prosthetic disc. The material or materials used in the end plates may be the same as or different than the materials used in the core. Often, the cast component will be adherent to at least one other disc component as a result of its flowing to and contact with that at least one other component of the prosthetic disc, but need not be adherent unless we specifically so state or the circumstances of the discussion require it.

By "flowable," we mean to include pastes, suspensions, and liquids that will flow into open molds such as those described below without the need for either pressure or vacuum, materials that will move into those molds with vacuum or pressurization, thixotropic materials, and other materials with non-Newtonian flow characteristics.

Typically, such "flowing" and "forming a non-flowable material" will be carried out at a temperature within the range of about 50° F. to about 125° F. because of the materials found in the other components. That is to say, for instance, that a chosen epoxy casting material will enter the mold and there form a material that does not flow (i.e., "cure" or "polymerize") at body temperature. Curing the flowable material at room temperature is a good choice where the core comprises an elastomer or a gel. Such a choice of casting temperatures would be dependent upon wise design choices due to, e.g., the composition of the other materials in the prosthetic disc. We will refer to castability in this temperature range as being "room temperature castability."

Higher casting temperatures would be suitable if the other materials in the disc were suitably chosen. For instance, thermoplastics that are flowable at high temperatures (e.g., polyolefins that are injection molded at 450° F.) would be acceptable if the remainder of the disc were metallic. We will refer to castability in the temperature range above 125° F. as being "high temperature castability."

In general, selected castable, biocompatible epoxies (two-part, one-part, or ultraviolet-light curable) are suitable for the cast parts, in particular the endplate or endplates. Such epoxies are commercially available from Ciba Specialty Chemicals (Basel, Switzerland), Master Bond Inc. (Hackensack, N.J.), and others. Other castable polymers are also suitable, including certain polyurethanes, polyesters, and polyacrylics. Implant grade polyurethanes such as those commercially available from the Polymer Technology Group or Cardiotech are suitable in some of our variations. Other chosen members of functional polymer classes such as thermoplastic elastomers (TPE's), elastomers, and silicones are suitable. Generically, when we speak broadly of such polymers, we include in the material referred to, such adjuvants or modifiers as fillers (minerals, polymeric fibers, metal or alloy powders such as silver for conductivity or tantalum or tungsten for radio-opacity), thickeners, thinners, accelerators, adhesion promoters, flexibilizers, wetting agents, etc.). Medicinal adjuvants such as bone-growth enhancers, antibiotics, etc. are also in that class of materials considered as integrated into the generic polymer class.

If an end plate is not fabricated from a flowable material, that component may be fabricated from physiologically acceptable materials having appropriate mechanical properties, such as titanium, titanium alloys, stainless steel, cobalt/chromium, etc.; polymers such as ultra high molecular weight polyethylene (UHMW-PE), polyether ether ketone (PEEK), etc.; ceramics; graphite; etc. Components of the cast end plates not fabricated of the cast material may also be comprised of the materials listed just above.

Figure 8:
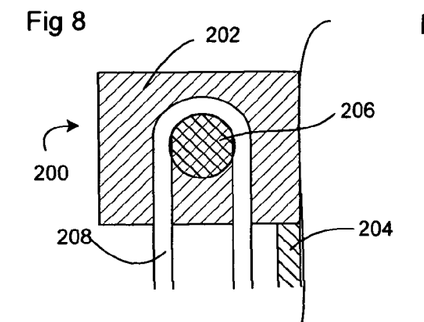
FIGS. 8-15 show cross-section side views of portions of component endplates and depict various ways in which the end plates are affixed to peripheral core members via casting.

FIG. 8 shows a cross-section of a portion of a prosthetic disc 200 having a cast end plate 202, a central core member 204, a bead member 206, and a fibrous member 208. The bead member 206 and the fiber member 208 are similar in form to those similarly named components in FIG. 6. In this variation, the fiber member 208 is affixed in the cast end plate 202. The bead member 206 provides a physical site for enhanced support of the fiber member 208. As will explained below with respect to FIG. 16, the bead member 206 and the fibrous member 208 may be positioned in the cast end plate 202 prior to the curing or hardening of the polymeric material in the cast end plate 202 and the fiber member (or members) may be pre-stressed or biased during that curing step. In this variation, the fiber member 208 forms the peripheral core member discussed above.

Figure 9:
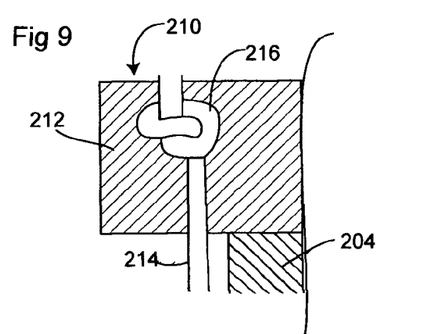

FIG. 9 shows a cross-section of a portion of another variation of our prosthetic disc 210 having a cast end plate 212, a central core member 204, and a fibrous member 214. In this instance, the fiber member 214 includes a knot 216 to provide mechanical fixation within cast end plate 212 in addition to any adhesive fixation found between the fibrous member 214 and the cast end plate 212. In this variation, the fiber member 214 forms the peripheral core member.

Figure 10:
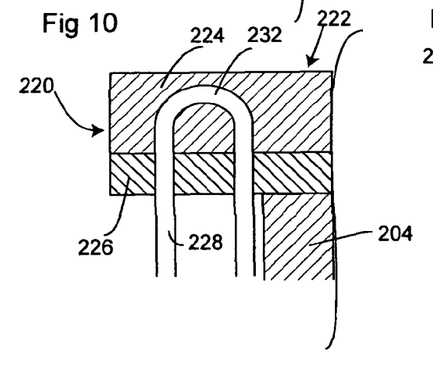

FIG. 10 shows a cross-section of a portion of another variation of our prosthetic disc 220 having a layered cast end plate 222 (having an upper layer 224 and a lower layer 226), a central core member 204, and a looped fibrous member 228. In this variation the cast end plate 222 is formed in a sequence of steps that allows the loop 232 to provide mechanical fixation between the fibrous member 228 and the cast end plate 222. The fiber member 228 also participates in any adhesive fixation with the cast end plate 222. To form the layered cast end plate 222, the fiber member 228 is first held so that the loop 232 is formed and is maintained while casting material flows into a mold forming thin inner layer 226. After the lower layer 226 is cured and adheres to fiber member 228, additional flowable material flows into a mold situated to allow flowable material for upper layer 224 to accumulate to the level shown in the Figure, above the crest of the loop 232. In this variation, the fiber member 228 forms the peripheral core member.

Figure 11:
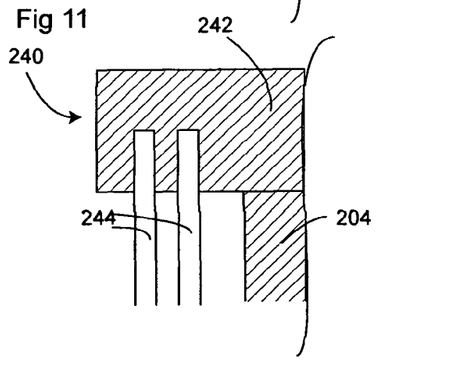

FIG. 11 shows a cross-section of a portion of still another variation of our prosthetic disc 240 having a cast end plate 242, a central core member 204, and multiple fibrous members 244. Fiber members 244 simply form stubs within cast end plate 242 and rely upon adhesive fixation between the fibrous members 244 and the cast end plate 242. The fibers 244 may be treated to enhance the adhesion with the materials of the cast end plate 242. In this variation, the fiber members 244 form the peripheral core member.

Figure 12:
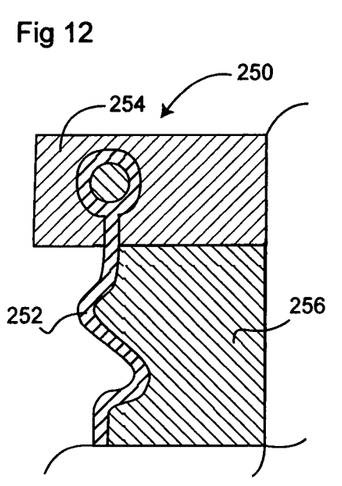

FIG. 12 shows a cross-section of a portion of a variation of our prosthetic disc 250. The peripheral core member comprises a metallic corrugated band 252 that is affixed within end plate 254. In this variation, the inner core 256 may be molded within the volume formed by the end plate 254, band 252, and the end plate at the opposing end of the disc 250 from end plate 254. Of course, the inner core 256 may be introduced into the disc 250 prior to forming the end plate 254.

Figure 13:
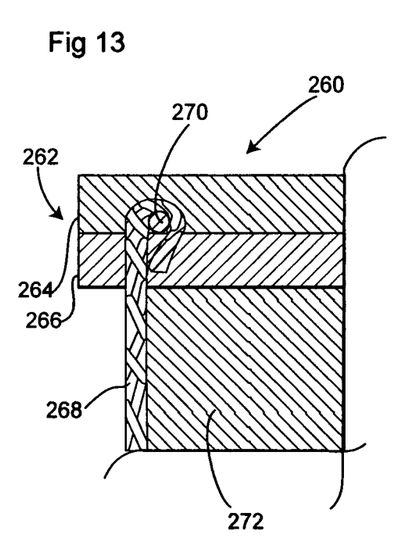

FIG. 13 shows a cross-section of a portion of a variation of our prosthetic disc 260. The end plate 262 comprises an upper layer 264 and a lower layer 266. The dual layer end plate 262 may be made in the same way as that discussed with regard to FIG. 10. The prosthetic disc 260 further comprises a fabric or fiber-containing membrane 268 (of a form similar to that shown in FIG. 7) that may be wrapped or rolled around a bead member 270. The core member 272 may be a gel or elastomeric material. The fabric or fiber-containing membrane 268 forms the peripheral core member.

FIG. 14 shows a cross-section of a portion of a variation of our prosthetic disc 280 with a cast end plate 282. The peripheral core member comprises pre-wrapped or pre-wound core member 284 having a multi-fiber winding 286 optionally covered with an additional polymeric layer 288. In this variation, the inner core 284 is placed within a mold and flowable material added to form the depicted cast end plate 282. The inner core 284 adheres to the cast end plate 282.

Figure 15:
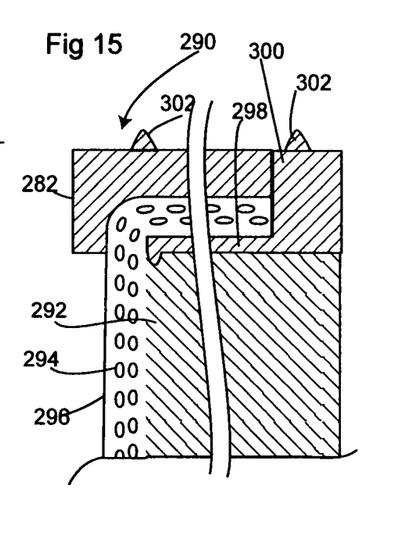

Finally, FIG. 15 shows a cross-section of a portion of a variation of our prosthetic disc 290 with a cast end plate 282 situated about a pre-wound core member 292 having a multi-fiber winding 294 with an additional exterior polymeric layer 296. The core member 292 further comprises an inner end plate 298 with an extension post 300 allowing additional adhesive connection to the cast end plate 282. This variation of the prosthetic disc 290 is configured to connect directly to adjacent vertebrae and includes barbed keels 302.

Figure 16:
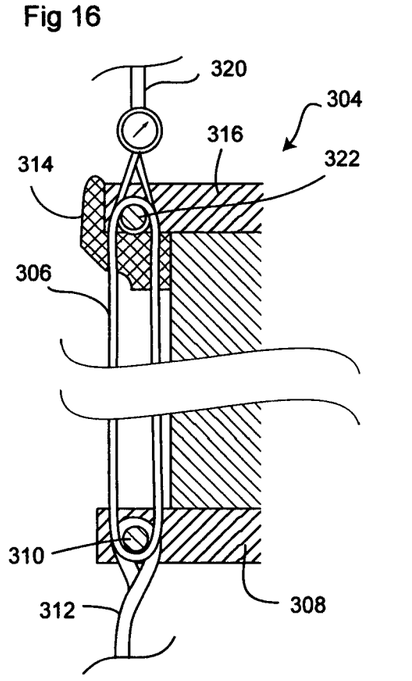
FIG. 16 shows a molding or casting arrangement for positioning the casting material while assembling a prosthetic disc and further shows a step for inducing a bias or pre-stress on fiber components of a peripheral core member.

FIG. 16 shows a manner of producing our prosthetic disc 304 and of pre-stressing the fibers 306 forming the peripheral core member. In this depiction, the lower end plate 308 with bead member 310 has already been cast. Static attachment 312 is attached to bead member 310 but is later removable.

At the upper end of the disc 304, a mold 314 provides a shape for forming upper end plate 316. The mold 314 may be comprised of a removable wax that may be later removed after the upper end plate 316 has cured. Suitable casting waxes (e.g., Protowax from Kindt-Collins Company LLC, Cleveland, Ohio) are readily available. Stress is placed on the fibers 306 via pull 320. As the stress is increased on pull 320, bead member 322 will rise in the castable material in upper plate 316 (at least as long as the material is fluid) and place a pre-stress on the fiber 306. Once the upper plate 316 is cured, the upper pull 320 is released as is the lower static attachment 312.

In general, our prosthetic devices are deployed by first removing a natural disc from a patient's spine to produce a disc void space. The prosthetic disc is then implanted or positioned in the disc void space, thereby, in effect, replacing the removed disc with the prosthetic disc. This implantation procedure may include the implantation of a vertebral body fixation element. Further steps may include, as needed, a post implantation vertebral body securing step, or other variations, depending on the particular configuration of the prosthetic device being employed.

Our prosthetic discs are able to approach or to mimic the mechanical properties of the fully functional natural discs that they are intended to replace. In particular, spinal motions may be characterized as compression, shock absorption, flexion (forward) and extension (backward), lateral bending (side-to-side), torsion (twisting), translation, and sublaxation. The described prosthetic discs are able to controllably constrain each such motion and to closely mimic the performance of natural discs.

We claim as our invention:

1. A prosthetic intervertebral disc comprising:
    a.) first and second end plates, wherein at least one of the end plates is a cast end plate, and
    b.) a compressible core member positioned between said first and second end plates and formed prior to casting of the at least one cast end plate, the compressible core member being wound with fibers that extend between and engage both the first and second end plates, and wherein the at least one cast end plate comprises a cast polymer having a form provided by causing the polymer to flow to the fibers of the wound compressible core member, by causing the polymer to solidify, and thereby casting the at least one cast end plates.

2. The prosthetic intervertebral disc of claim 1 wherein the cast polymer comprises an epoxy, polyurethane, polyester, polyacrylic, or their mixtures and alloys.

3. The prosthetic intervertebral disc of claim 1 wherein the compressible core member comprises at least one material selected from hydrogels, elastomers, and thermoplastic elastomers.

4. A prosthetic intervertebral disc comprising:
    a.) first and second end plates, wherein at least one of the end plates is a cast end plate, and
    b.) a compressible core member positioned between said first and second end plates and formed prior to casting of the at least one cast end plate, wherein the compressible core member further comprises a peripheral core member extending between and engaging the first and second end plates and wherein the peripheral core member is made to engage the at least one cast end plate, and wherein the at least one cast end plate is formed by causing the polymer to flow to the peripheral core member, causing the polymer to cure and thereby casting the least one cast end plate and thereby further causing the peripheral core member to engage the at least one cast end plate.

5. The prosthetic intervertebral disc of claim 4 wherein the peripheral core member is made to engage both the first and the second end plates by causing the polymer to flow to the peripheral core member, causing the polymer to solidify, and thereby casting first and second cast end plates.

6. The prosthetic intervertebral disc of claim 5 wherein the peripheral core member comprises at least one fiber extending between and engaging the first and the second end plates.

7. The prosthetic intervertebral disc of claim 6 wherein the peripheral core member further comprises a bead member cast into each of the first and the second cast end plates.

8. The prosthetic intervertebral disc of claim 5 wherein the peripheral core member comprises a fiber-containing membrane extending between and engaging the first and the second end plates.

9. The prosthetic intervertebral disc of claim 8 wherein the peripheral core member further comprises a bead member cast into each of the first and the second cast end plates.

10. The prosthetic intervertebral disc of claim 4 wherein the peripheral core member comprises at least one fiber extending between and engaging the first and the second end plates.

11. The prosthetic intervertebral disc of claim 10 wherein the peripheral core member further comprises at least one bead member cast into the at least one first and the second cast end plates.

12. The prosthetic intervertebral disc of claim 4 wherein the peripheral core member further comprises a metallic stent-like member cast into the at least one first and the second cast end plates.

13. The prosthetic intervertebral disc of claim 12 wherein both the first and second end plates comprise cast end plates and wherein the peripheral core member comprises a metallic stent-like member cast into each of the first and the second cast end plates.

14. The prosthetic intervertebral disc of claim 4 wherein the peripheral core member comprises a fiber-containing membrane extending between and engaging the first and the second end plates.

15. The prosthetic intervertebral disc of claim 14 wherein the peripheral core member further comprises at least one bead member cast into the at least one first and the second cast end plates.

16. A prosthetic intervertebral disc comprising:
a first end plate,
a second end plate, and
a compressible core member positioned between said first and second end plates wherein at least one of the end plates is a cast end plate, and
a peripheral core member positioned substantially peripheral to the compressible core member and extending between the first and second end plates and formed prior to casting of the at least one cast end plate, and
wherein the at least one cast end plate comprises a cast polymer, and wherein the peripheral core member is made adherent to the at least one cast end plate by causing that polymer to flow to the peripheral core member, causing the polymer to cure and thereby casting the at least one cast end plate and further thereby causing the peripheral core member to adhere to the at least one cast end plate.

17. The prosthetic intervertebral disc of claim 16 wherein the cast polymer comprises an epoxy, polyurethane, polyester, polyacrylic, or their mixtures or alloys.

18. The prosthetic intervertebral disc of claim 16 wherein the compressible core member comprises at least one material selected from hydrogel, elastomer, and thermoplastic elastomer.

* * * * *